United States Patent
Cai et al.

(10) Patent No.: US 6,599,900 B2
(45) Date of Patent: Jul. 29, 2003

(54) 1-OXA-3,9-DIAZA-SPIRO[5,5]UNDECAN-2-ONES

(75) Inventors: Hai-Ying Cai, Cupertino, CA (US); Michael Patrick Dillon, San Carlos, CA (US); Guido Galley, Rheinfelden (DE); Annick Goergler, Colmar (FR); Sabine Kolczewski, Rheinfelden (DE); Dawn Muszynski Barsy, Cupertino, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/143,431

(22) Filed: May 10, 2002

(65) Prior Publication Data

US 2003/0004163 A1 Jan. 2, 2003

(30) Foreign Application Priority Data

May 14, 2001 (EP) .............................................. 01111644

(51) Int. Cl.⁷ ..................... C07D 498/10; A61K 31/535
(52) U.S. Cl. ...................... 514/230.5; 544/91
(58) Field of Search ........................ 544/91; 514/230.5

(56) References Cited

FOREIGN PATENT DOCUMENTS

| GB | 2 131 021 A | 6/1984 |
|---|---|---|
| WO | WO 95/16679 A1 | 6/1995 |
| WO | WO 97/11940 A1 | 4/1997 |

*Primary Examiner*—Bruck Kifle
(74) *Attorney, Agent, or Firm*—Robert C. Hall; Rohan Peries

(57) ABSTRACT

The invention relates to compounds of the general formula

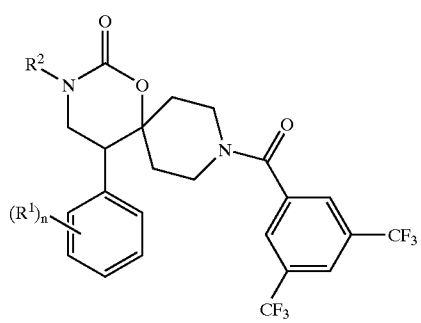

I wherein ($R^1$)$_n$ is independently from from each other halogen, lower alkyl or lower alkoxy;

$R^2$ is hydrogen, lower alkyl, lower halogen-alkyl, —(CH$_2$)$_m$—OH, —(CH$_2$)$_m$—NR$_2$, —(CH$_2$)$_m$O-lower alkyl, —(CH$_2$)$_m$—C(O)—NR$_2$, or is —(CH$_2$)$_m$-6-membered heteroaryl, optionally substituted by one or more lower alkoxy, —(CH$_2$)$_m$-5 or 6-membered not aromatic heterocyclyl, optionally substituted by hydroxy or lower alkyl;

R is hydrogen or lower alkyl and may be the same or different in case of $R_2$;

n is 0, 1, or 2;

m is 0, 1, 2, 3 or 4;

and pharmaceutically acceptable acid addition salts thereof. These compounds have a good affinity to the NK-1 receptor and they are therefore suitable for the treatment of diseases, related to this receptor.

16 Claims, No Drawings

1-OXA-3,9-DIAZA-SPIRO[5,5]UNDECAN-2-ONES

CROSS REFERENCE TO RELATED APPLICATION

This application claims benefit under Title 35, United States Code, §119 of European Patent Application No. 01111644.9, filed May 14, 2001.

BACKGROUND OF THE INVENTION

Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The neuropeptide receptor for substance P (NK-1) is widely distributed throughout the mammalian nervous system (especially brain and spinal ganglia), the circulatory system and peripheral tissues (especially the duodenum and jejunum) and are involved in regulating a number of diverse biological processes. The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases reviewed in "Tachykinin Receptor and Tachykinin Receptor Antagonists", J. Auton. Pharmacol., 13, 23–93, 1993.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, in The New England Journal of Medicine, Vol. 340, No. 3 190–195, 1999 has been described the reduction of cisplatin-induced emesis by a selective neurokinin-1-receptor antagonist.

Furthermore, U.S. Pat. No. 5,972,938 describes a method for treating a psychoimmunologic or a psychosomatic disorder by administration of a tachykinin receptor, such as NK-1 receptor antagonist.

The usefulness of neurokinin 1 receptor antagonists for the treatment of certain forms of urinary incontinence is further described in "Neuropeptides, 32(1), 1–49, (1998)" and "Eur. J. Pharmacol., 383(3), 297–303, (1999)".

NK1 receptor antagonists have been reported to have also a beneficial effect in the therapy of traumatic brain injury (oral disclosure by Prof. Nimmo at the International Tachykinin Conference 2000 in La Grande Motte, France, Oct. 17–20, 2000 with the title "Neurokinin 1 (NK-1) Receptor Antagonists Improve the Neurological Outcome Following Traumatic Brain Injury" (Authors: A. J. Nimmo, C. J. Bennett, X. Hu, I. Cernak, R. Vink)."

SUMMARY OF THE INVENTION

The present invention relates to compounds of the general formula

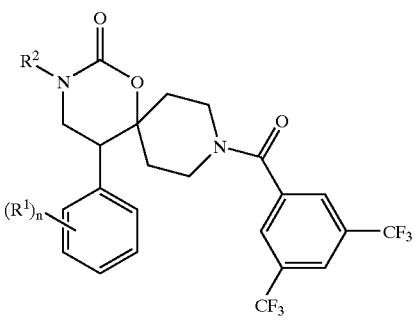

wherein
$(R^1)_n$ is independently from each other halogen, lower alkyl or lower alkoxy;
$R^2$ is hydrogen, lower alkyl, lower halogen-alkyl, —$(CH_2)_m$—OH, —$(CH_2)_m$—$NR_2$, —$(CH_2)_m$O-lower alkyl, —$(CH_2)_m$—C(O)—$NR_2$, or is —$(CH_2)_m$-6-membered heteroaryl, optionally substituted by one or more lower alkoxy, —$(CH_2)_m$-5 or 6-membered not aromatic heterocyclyl, optionally substituted by hydroxy or lower alkyl;
R is hydrogen or lower alkyl and may be the same or different in case of $R_2$;
n is 0, 1, or 2;
m is 0, 1, 2, 3 or 4;
and to pharmaceutically acceptable acid addition salts thereof The compounds of formula I and their salts are characterized by valuable therapeutic properties. It has been surprisingly found that the compounds of the present invention are antagonists of the Neurokinin 1 (NK-1, substance P) receptor.

DETAILED DESCRIPTION OF THE INVENTION

The present invention relates to compounds of formula I and pharmaceutically acceptable salts thereof, the preparation of the above-mentioned compounds, medicaments containing them and their manufacture as well as the use of the above-mentioned compounds in the control or prevention of illnesses, especially of illnesses and disorders of the kind referred to earlier or in the manufacture of corresponding medicaments.

The compounds of formula I can also be used in form of their prodrugs. Examples are esters, N-oxides, phosphate esters, glycoamide esters, glyceride conjugates and the like. The prodrugs may add to the value of the present compounds advantages in adsorption, pharmacokinetics in distribution and transport to the brain.

The most preferred indications in accordance with the present invention are those, which include disorders of the central nervous system, for example the treatment or prevention of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

The following definitions of the general terms used in the present description apply irrespective of whether the terms in question appear alone or in combination.

As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like. Preferred lower alkyl groups are groups with 1–4 carbon atoms.

The term "halogen-lower alkyl" denotes a lower alkyl group, wherein one or more hydrogen atom(s) is/are replaced by halogen.

The term "lower alkoxy" denotes a group wherein the alkyl residues are as defined above, and which is attached via an oxygen atom.

The term "halogen" denotes chlorine, iodine, fluorine and bromine.

The term "6-membered heteroaryl" denotes groups, such as triazinyl, pyridinyl, pyrazinyl, pyrimidinyl or pyridazinyl. Preferred are triazinyl- and pyridinyl groups.

The term "5 or 6-membered non aromatic heterocyclyl" denotes groups, such as pyrrolidinyl, imidazolidinyl, tetrahydro-pyranyl, piperidyl, piperazinyl or morpholinyl. Preferred are piperazinyl-, morpholinyl-, piperidyl-, tetrahydro-pyranyl- and pyrrolidinyl-groups.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

Exemplary preferred are compounds of formula 1, in which $R^2$ is hydrogen, for example the following compounds:

(5RS)-9-(3,5-bis-trifluoromethyl-benzoyl)-5-(3-chlorophenyl)-1-oxa-3,9-diaza-spiro[5.5]undecan-2-one,
(5RS)-9-(3,5-bis-trifluoromethyl-benzoyl)-5-(3,4-difluorophenyl)-1-oxa-3,9-diaza-spiro[5.5]undecan-2-one,
(5RS)-9-(3,5-bis-trifluoromethyl-benzoyl)-5-(3,4-dichlorophenyl)-1-oxa-3,9-diaza-spiro[5.5]undecan-2-one,
(5RS)-9-(3,5-bis-trifluoromethyl-benzoyl)-5-phenyl-1-oxa-3,9-diaza-spiro[5.5]undecan-2-one,
(5RS)-9-(3,5-bis-trifluoromethyl-benzoyl)-5-(2,3-difluorophenyl)-1-oxa-3,9-diaza-spiro[5.5]undecan-2-one and
(5RS)-9-(3,5-bis-trifluoromethyl-benzoyl)-5-(2,5-difluorophenyl)-1-oxa-3,9-diaza-spiro[5.5]undecan-2-one.

Further preferred are compounds of formula I, wherein $R^2$ is a —$(CH_2)_m$-6-membered heteroaryl group, optionally substituted by one or more lower alkoxy. Examples of such compounds are:

(5RS)-9-(3,5-bis-trifluoromethyl-benzoyl)-5-phenyl-3-pyridin-3-yl-methyl-1-oxa-3,9-diaza-spiro[5.5]undecan-2-one and
(5RS)-9-(3,5-bis-trifluoromethyl-benzoyl)-3-(4,6-dimethoxy-[1,3,5]triazin-2-yl)-5-phenyl-1-oxa-3,9-diaza-spiro[5.5]undecan-2-one.

Further preferred are compounds of formula I, wherein $R^2$ is —$(CH_2)_m$—C(O)—N(CH_3)_2$. An examples of such compounds is:

(5RS)-2-[9-(3,5-bis-trifluoromethyl-benzoyl)-2-oxo-5-phenyl-1-oxa-3,9-diaza-spiro[5.5]undec-3-yl]-N,N-dimethyl-acetamide.

Further preferred are compounds of formula I, wherein $R^2$ is —$(CH_2)_m$—OH. Examples of such compounds are:

(5RS)-9-(3,5-bis-trifluoromethyl-benzoyl)-3-(3-hydroxypropyl)-5-phenyl-1-oxa-3,9-diaza-spiro[5.5]undecan-2-one and
(5RS)-9-(3,5-bis-trifluoromethyl-benzoyl)-3-(2-hydroxyethyl)-5-phenyl-1-oxa-3,9-diaza-spiro[5.5]undecan-2-one.

Further preferred are compounds of formula I, wherein $R^2$ is a —$(CH_2)_m$-5 or 6-membered not aromatic heterocyclyc group, optionally substituted by hydroxy or lower alkyl. Examples of such compounds are:

(5RS)-9-(3,5-bis-trifluoromethyl-benzoyl)-3-(1-methyl-piperidin-4-yl)-5-phenyl-1-oxa-3,9-diaza-spiro[5.5] undecan-2-one,
(5RS)-9-(3,5-bis-trifluoromethyl-benzoyl)-5-phenyl-3-(3-pyrrolidin-1-yl-propyl)-1-oxa-3,9-diaza-spiro[5.5] undecan-2-one,
(5RS)-9-(3,5-bis-trifluoromethyl-benzoyl)-3-(3-morpholin-4-yl-propyl)-5-phenyl-1-oxa-3,9-diaza-spiro[5.5] undecan-2-one,
(5RS)-9-(3,5-bis-trifluoromethyl-benzoyl)-3-[3-(3-hydroxy-pyrrolidin-1-yl)-propyl]-5-phenyl-1-oxa-3,9-diaza-spiro[5.5]undecan-2-one and
(5RS)-9-(3,5-2is-trifluoromethyl-benzoyl)-3-(2-morpholin-4-yl-ethyl)-5-phenyl-1-oxa-3,9-diaza-spiro[5.5]undecan-2-one.

Further preferred are compounds of formula I, wherein $R^2$ is —$(CH_2)_m$—NR_2$. Examples of such compounds are:

(5RS)-9-(3,5-bis-trifluoromethyl-benzoyl)-3-(3-dimethylamino-4-yl-propyl)-5-phenyl-1-oxa-3,9-diaza-spiro[5.5]undecan-2-one and (5RS)-9-(3,5-bis-trifluoromethyl-benzoyl)-3-(2-dimethylamino-ethyl)-5-phenyl-1-oxa-3,9-diaza-spiro[5.5]undecan-2-one.

The present compounds of formula I and their pharmaceutically acceptable salts can be prepared by methods known in the art, for example, by processes described below, which process comprises a) cyclizing a compound of formula

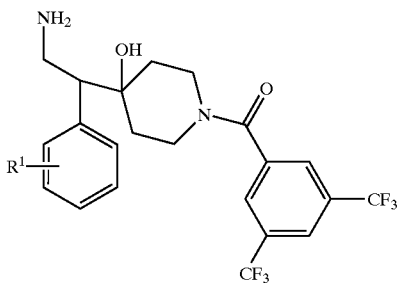

to a compound of formula

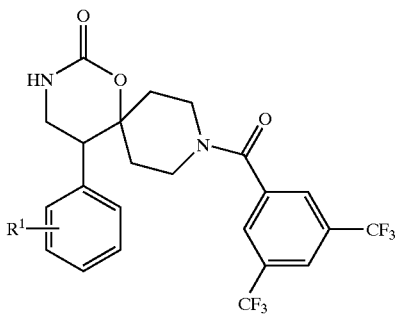

wherein R¹ has the significances given above, or b) reacting a compound of formula

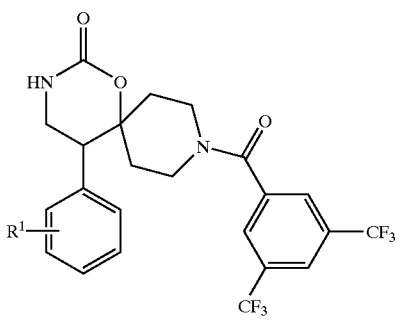

with

R²—X to a compound of formula

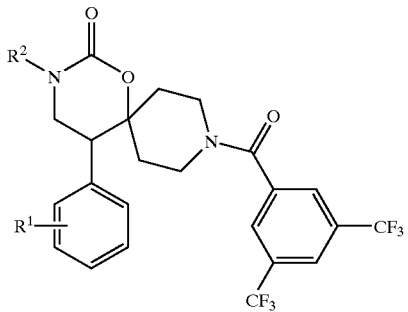

wherein R¹ and R² have the significances given above and X is halogen, or c) reacting a compound of formula

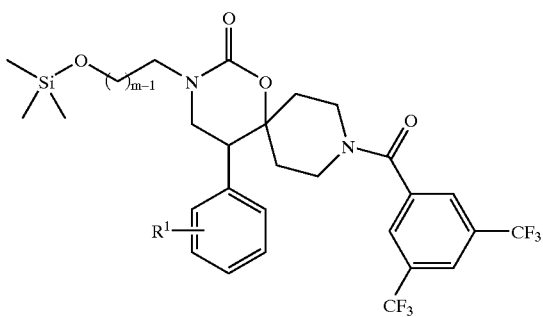

to a compound of formula

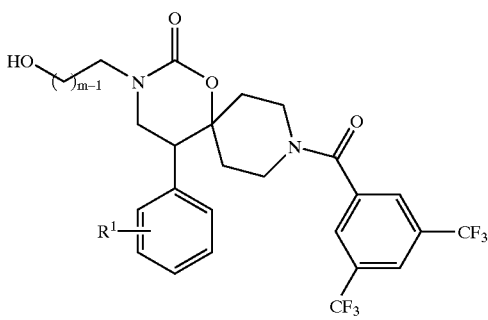

and wherein m and R¹ are described above, or d) reacting a compound of formula

Ib

HO_____/N\_\_\_ with a compound of formula

R₂NH to a compound of formula

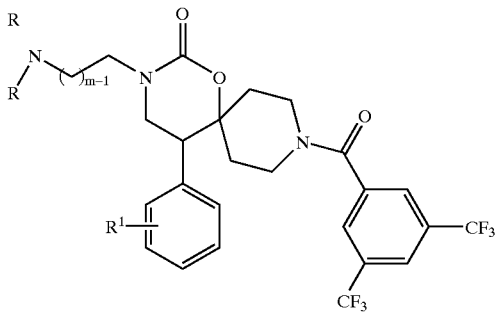

Ib wherein the definition for R¹ is given above, and R is hydrogen or lower alkyl, or e) reacting a compound formula

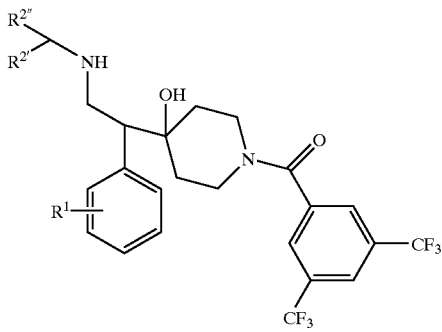

III to a compound of formula

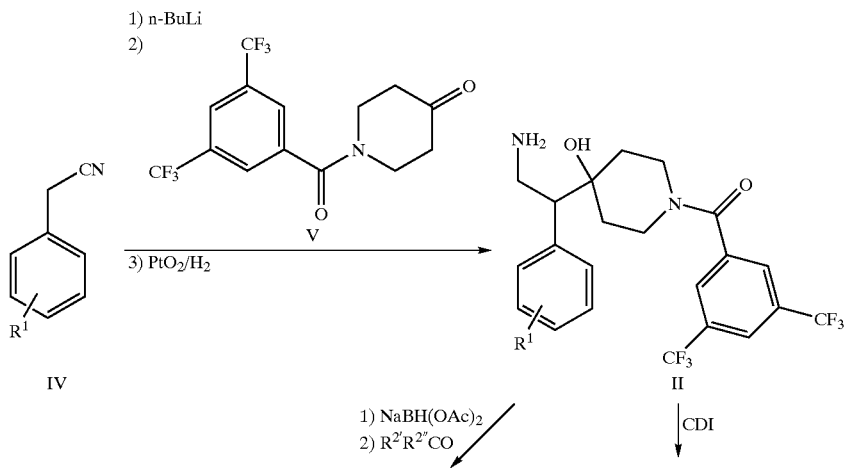

Id wherein R¹ is described above and R²' and R²'' are independently from each other hydrogen, alkyl, aryl, heteroaryl or taken together a not aromatic carbocyclic or heterocyclic ring, optionally substituted by halogen, hydroxy, lower alkoxy or hydroxy or lower alkyl, and if desired, converting the compound obtained into a pharmaceutically acceptable acid addition salt.

The following scheme and specific examples 1 to 30 describe the processes for preparation of compounds of formula I in more detail. The starting materials are known compounds and may be prepared according to methods known in the art.

-continued
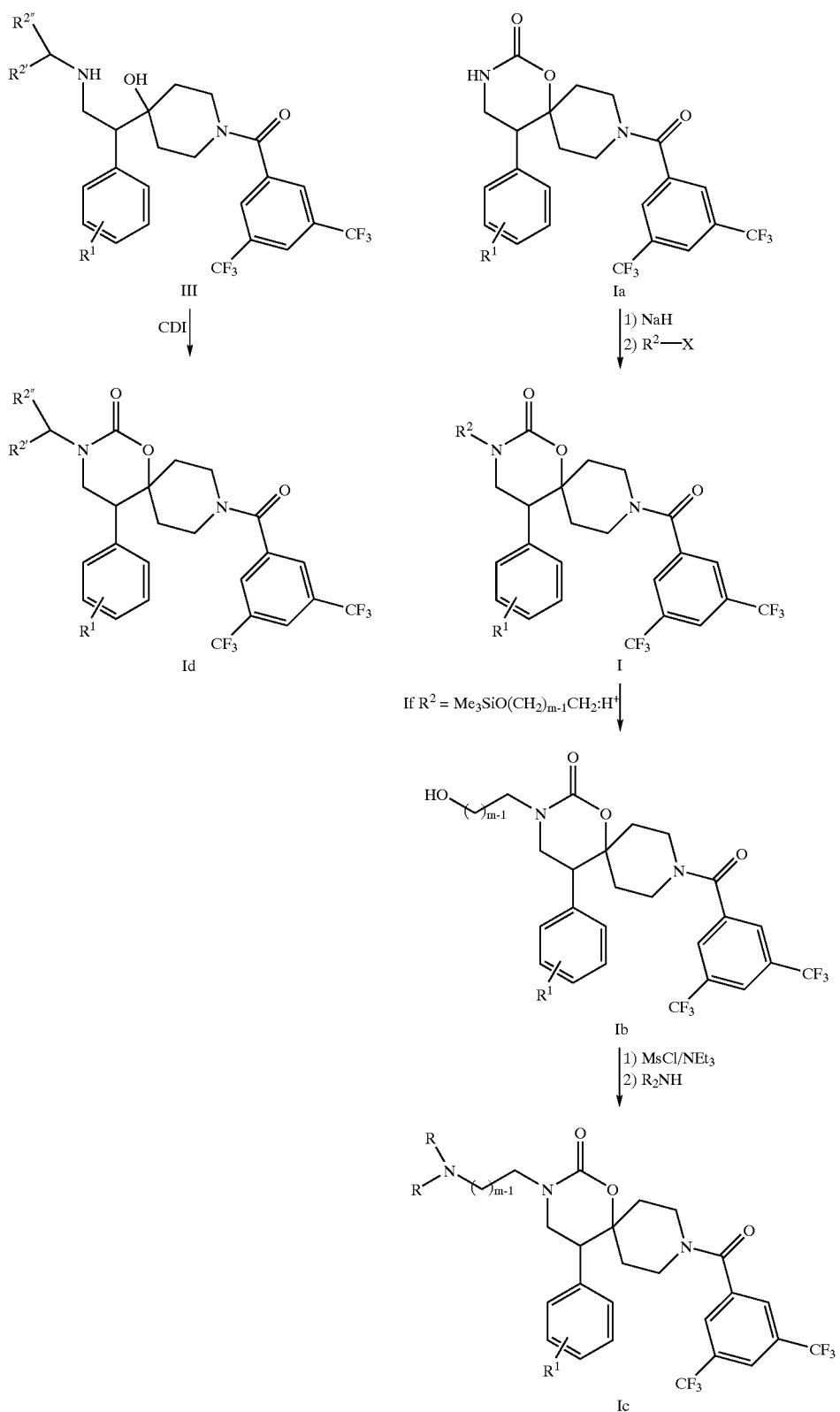
CDI = 1,1'-carbonyl-diimidazole
MsCl = methanesulfonyl chloride wherein in this scheme $R^{2'}$ and $R^{2''}$ are independently from each other hydrogen, alkyl, aryl, heteroaryl or taken together a not aromatic carbocyclic or heterocyclic ring, optionally substituted by halogen, hydroxy, lower alkoxy, hydroxy or lower alkyl.

In accordance with the scheme above, a compound of formula IV is treated with n-butyllithium in tetrahydrofuran at −78° C. for 30 min then a compound V is added and the mixture is stirred at −78° C. for 4 hours. The crude product obtained after work-up is hydrogenated in the presence of $PtO_2$ in acetic acid at 2.7 bar. The desired compound of formula II is obtained without purification in moderate to good yields.

A compound of formula II is cyclised to give a compound of formula Ia. The reaction is carried out in a solvent such as tetrahydrofuran in the presence of 1,1'-carbonyl-diimidazole. The reaction mixture is stirred at room temperature for about 18 hours. The desired product was obtained after purification in good yields.

The compound of formula Ia is deprotonated with NaH (sodium hydride 55% in mineral oil) at room temperature in dimethylformamide, dimethoxyethane or N-methylpyrrolidine for 15 min and an alkylating reagent is added. The reaction mixture is stirred at room temperature or at 80° C. or at 100° C. overnight. The desired compound of formula I is obtained after purification by column chromatography.

A compound of formula I ($R^2=Me_3SiO(CH_2)_{m-1}$—$CH_2$—) is deprotected under acidic conditions to give a compound of formula Ib without purification.

According to example 23, a compound of formula Ib is treated with methanesulfonyl chloride in dichloromethane at 0° C. in presence of triethylamine for 90 min. After work-up, the intermediate methanesulfonate is dissolved in dimethylformamide and sodium hydrogencarbonate and an amine is added. The reaction mixture is stirred overnight at room temperature. The desired product of formula Ic is obtained after purification by column chromatography.

The salt formation is effected at room temperature in accordance with methods which are known.

Example 12, process b) describes the reductive amination reaction of a compound of formula II with a ketone to a compound of formula III. The reaction is carried out in presence of sodium triacetoxyborohydride and acetic acid. The mixture is stirred at room temperature overnight. The desired product is directly used for the next step without purification.

A compound of formula III is cyclised in a solvent such as tetrahydrofuran in presence of 1,1'-carbonyl-diimidazole to give a compound of formula Id. The reaction mixture is stirred at room temperature for about 18 hours. The desired product was obtained after purification in good yields.

The process for preparation of compounds of formula I, described in scheme 1, is novel. The preparation of similar compounds have been described in Eur. J. Med. Chem.—Chim. Ther. (1974), 9(4), 416–23 as follows:

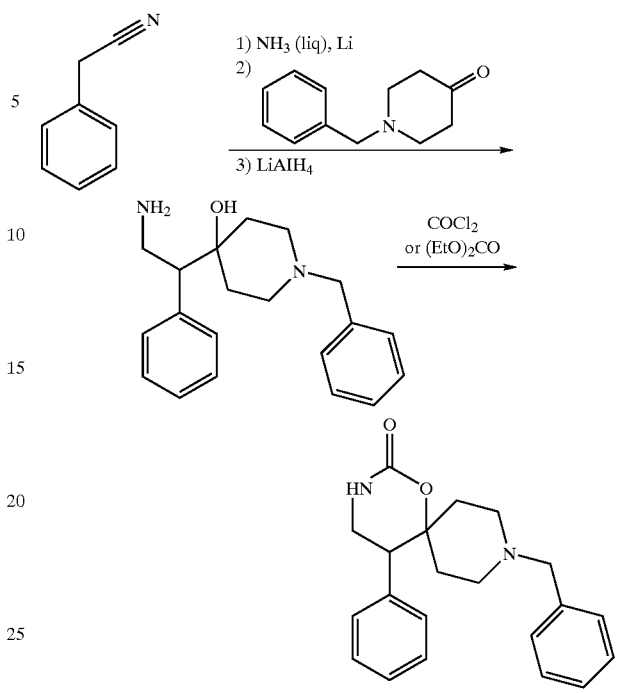

After debenzylation a reaction with $(CF_3)_2C_6H_3$—C(O)Cl leads to compounds of the present formula I.

The salt formation is effected at room temperature in accordance with methods which are known per se and which are familiar to any person skilled in the art. Not only salts with inorganic acids, but also salts with organic acids may also be used. Hydrochlorides, hydrobromides, sulphates, nitrates, citrates, acetates, maleates, succinates, methansulphonates, p-toluenesulphonates and the like are examples of such salts.

As mentioned earlier, the compounds of formula I and their pharmaceutically usable addition salts possess valuable pharmacological properties. It has been found that the compounds of the present invention are antagonists of the Neurokinin 1 (NK-1, substance P) receptor.

The compounds were investigated in accordance with the tests given hereinafter.

The affinity of test compounds for the $NK_1$ receptor was evaluated at human $NK_1$ receptors in CHO cells infected with the human $NK_1$ receptor (using the Semliki virus expression system) and radiolabelled with [$^3$H]substance P (final concentration 0.6 nM). Binding assays were performed in HEPES buffer (50 mM, pH 7.4) containing BSA (0.04%) leupeptin (8 µg/ml), $MnCl_2$ (3 mM) and phosphoramidon (2 µM). Binding assays consisted of 250 µl of membrane suspension (1.25×10$^5$ cells/assay tube), 0.125 µl of buffer of displacing agent and 125 µl of [$^3$H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

The affinity to the NK-1 receptor, given as pKi, is in the scope of 7.50–8.80 for the compounds of formula I of the present invention.

| Example-No. | pKi | Example-No. | pKi |
|---|---|---|---|
| 1 | 8.29 | 16 | 8.21 |
| 2 | 8.77 | 17 | 7.88 |
| 3 | 8.58 | 18 | 7.81 |
| 4 | 8.29 | 19 | 7.72 |
| 5 | 8.07 | 20 | 7.51 |
| 6 | 8.01 | 21 | 8.17 |
| 7 | 7.97 | 22 | 7.80 |
| 8 | 7.96 | 23 | 8.47 |
| 9 | 7.90 | 24 | 8.46 |
| 10 | 7.83 | 25 | 8.46 |
| 11 | 7.63 | 26 | 8.39 |
| 12 | 8.41 | 27 | 8.20 |
| 13 | 7.72 | 28 | 8.13 |
| 14 | 8.18 | 29 | 7.98 |
| 15 | 7.94 | 30 | 7.94 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc. can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following Examples illustrate the present invention without limiting it. All temperatures are given in degrees Celsius.

EXAMPLE 1

(5RS)-9-(3,5-bis-trifluoromethyl-benzoyl)-5-(3-chloro-phenyl)-1-oxa-3,9-diaza-spiro[5.5]undecan-2-one a) (RS)-{4-[2-amino-1-(3-chloro-phenyl)-ethyl]-4-hydroxy-piperidin-1-yl}-(3,5-bis-trifluoromethyl-phenyl)-methanone To a solution of 3.392 g (10 mmol) 3-chlorobenzyl cyanide in tetrahydrofuran cooled at −78° C. 6.25 ml (10 mmol) n-butyllithium in n-hexan (1.6 M) was added slowly under argon. The solution was stirred for 30 min and 1-(3,5-bis-trifluoromethyl-benzoyl)-piperidin-4-one in tetrahydrofuran was dropped to the reaction mixture maintaining the temperature below −70° C. After stirring at −78° C. for 4 hours, the reaction mixture was poured into a mixture of ice/saturated aqueous $NH_4Cl$ and extracted with ethyl acetate. The organic layer was dried ($MgSO_4$) and concentrated under reduced pressure.

The crude material was dissolved in acetic acid and was hydrogenated in presence of $PtO_2$ at 2.7 bar. The catalyst was filtered off, water and hydrochloric acid (1 M) were added and the solution was extracted twice with dichloromethane. The aqueous phase was basified with concentrated sodium hydroxide and extracted twice with dichloromethane. The combined organic layers were dried and evaporated to give 2.21 g (46%) of the title compound.

MS m/e (%): 495.1 ($M+H^+$, 100).

b) (5RS)-9-(3,5-bis-trifluoromethyl-benzoyl)-5-(3-chloro-phenyl)-1-oxa-3,9-diaza-spiro[5.5]undecan-2-one To a solution of 1.48 g (3 mmol) {4-[2-amino-1-(3-chloro-phenyl)-ethyl]-4-hydroxy-piperidin-1-yl}-(3,5-bis-trifluoromethyl-phenyl)-methanone in 30 ml of tetrahydrofuran 1.46 g (9 mmol)1,1'-carbonyl-diimidazole was added and the mixture was stirred over night at room temperature under argon. Water (15 ml) was added, the organic layer was separated, washed twice with a solution of hydrochloric acid (1 M), dried and evaporated. The residue was purified by flash column chromatography ($SiO_2$, ethyl acetate) to yield 1.08 g (69%) of the title compound.

MS m/e (%): 521.0 ($M+H^+$, 100).

EXAMPLE 2

(5RS)-9-(3,5-bis-trifluoromethyl-benzoyl)-5-(3,4-difluoro-phenyl)-1-oxa-3,9-diaza-spiro[5.5]undecan-2-one The title compound was obtained in comparable yields according to the procedures described for example 1 using 3,4-difluorobenzyl cyanide instead of 3-chlorobenzyl cyanide in step a).

MS m/e (%): 523.1 ($M+H^+$, 100).

EXAMPLE 3

(5RS)-9-(3,5-bis-trifluoromethyl-benzoyl)-5-(3,4-dichloro-phenyl)-1-oxa-3,9-diaza-spiro[5.5]undecan-2-one The title compound was obtained in comparable yields according to the procedures described for example 1 using 3,4-dichlorobenzyl cyanide instead of 3-chlorobenzyl cyanide in step a)

MS m/e (%): 555.0 ($M+H^+$, 100), 557.0 ($M+H^+$, 60).

EXAMPLE 4

(5RS)-9-(3,5-bis-trifluoromethyl-benzoyl)-5-phenyl-1-oxa-3,9-diaza-spiro[5.5]undecan-2-one The title compound was obtained in comparable yields according to the procedures described for example 1 using benzyl cyanide instead of 3-chlorobenzyl cyanide in step a).

MS m/e (%): 487.2.0 (M+H$^+$, 100).

EXAMPLE 5

(5RS)-9-(3,5-bis-trifluoromethyl-benzoyl)-5-(2,3-difluoro-phenyl)-1-oxa-3,9-diaza-spiro[5.5]undecan-2-one The title compound was obtained in comparable yields according to the procedures described for example 1 using 2,3-difluorobenzyl cyanide instead of 3-chlorobenzyl cyanide in step a).

MS m/e (%): 523.1 (M+H$^+$, 100).

EXAMPLE 6

(5RS)-9-(3,5-bis-trifluoromethyl-benzoyl)-5-(2,5-difluoro-phenyl)-1-oxa-3,9-diaza-spiro[5.5]undecan-2-one The title compound was obtained in comparable yields according to the procedures described for example 1 using 2,5-difluorobenzyl cyanide instead of 3-chlorobenzyl cyanide in step a)

MS m/e (%): 140.0 (F$_2$C$_6$H$_3$CH═CH$_2$, 100); 522.1 (M$^+$, 3).

EXAMPLE 7

(5RS)-9-(3,5-bis-trifluoromethyl-benzoyl)-5-o-tolyl-1-oxa-3,9-diaza-spiro[5.5]undecan-2-one The title compound was obtained in comparable yields according to the procedures described for example 1 using 2-methylbenzyl cyanide instead of 3-chlorobenzyl cyanide in step a).

MS m/e (%):118.1 (CH$_3$C$_6$H$_4$CH═CH$_2$, 100); 501.2 (M+H$^+$, 2).

EXAMPLE 8

(5RS)-9-(3,5-bis-trifluoromethyl-benzoyl)-5-(4-chloro-phenyl)-1-oxa-3,9-diaza-spiro[5.5]undecan-2-one The title compound was obtained in comparable yields according to the procedures described for example 1 using 4-chlororobenzyl cyanide instead of 3-chlorobenzyl cyanide in step a).

MS m/e (%):138.0 (ClC$_6$H$_4$CH═CH$_2$, 100); 520.1 (M$^+$, 3).

EXAMPLE 9

(5RS)-9-(3,5-bis-trifluoromethyl-benzoyl)-5-(3,4-dimethyl-phenyl)-1-oxa-3,9-diaza-spiro[5.5]undecan-2-one The title compound was obtained in comparable yields according to the procedures described for example 1 using 3,4-dimethylbenzyl cyanide instead of 3-chlorobenzyl cyanide in step a).

MS m/e (%): 515.2 (M+H$^+$, 100).

EXAMPLE 10

(5RS)-9-(3,5-bis-trifluoromethyl-benzoyl)-5-(3-methoxy-phenyl)-1-oxa-3,9-diaza-spiro[5.5]undecan-2-one The title compound was obtained in comparable yields according to the procedures described for example 1 using 3-methoxybenzyl cyanide instead of 3-chlorobenzyl cyanide in step a).

MS m/e (%):134.1 (CH$_2$OC$_6$H$_4$CH═CH$_2$, 100); 516.2 (M$^+$, 3).

EXAMPLE 11

(5RS)-9-(3,5-bis-trifluoromethyl-benzoyl)-5-(2-chloro-phenyl)-1-oxa-3,9-diaza-spiro[5.5]undecan-2-one The title compound was obtained in comparable yields according to the procedures described for example 1 using 2-chlorobenzyl cyanide instead of 3-chlorobenzyl cyanide in step a).

MS m/e (%): 521.1 (M+H$^+$, 100).

EXAMPLE 12

(5RS)-9-(3,5-bis-trifluoromethyl-benzoyl)-3-(1-methyl-piperidin-4-yl)-5-phenyl-1-oxa-3,9-diaza-spiro[5.5]undecan-2-one a) (RS)-{[4-(2-amino-1-phenyl-ethyl)-4-hydroxy-piperidin-1-yl]-(3,5-bis-trifluoromethyl-phenyl)-methanone To a solution of 1.69 g (5 mmol) benzylcyanide in tetrahydrofurane cooled at −78° C. 3.75 ml (5 mmol) n-butyllithium in n-hexan (1.6 M) was added slowly under argon. The solution was stirred for 30 min and 1-(3,5-bis-trifluoromethyl-benzoyl)-piperidin-4-one in tetrahydrofurane was dropped to the reaction mixture maintaining the temperature below −70° C. After stirring at −78° C. for 2 hours, the reaction mixture was poured into a mixture of ice and saturated aqueous NH$_4$Cl and extracted with dichloromethane. The organic layer was dried (MgSO$_4$) and concentrated under reduced pressure.

The crude material was dissolved in acetic acid and was hydrogenated in presence of PtO$_2$ at 2.7 bar. The catalyst was filtered off, water and hydrochloric acid (1 M) were added and the solution was extracted twice with dichloromethane. The aqueous phase was basified with concentrated sodium hydroxide and extracted twice with dichloromethane The combined organic layers were dried and evaporated. The residue was purified by column chromatography (SiO$_2$, dichloromethane/methanol=90:10) to yield 0.73 g (34%) of the title compound.

MS m/e (%): 461.2 (M+H$^+$, 100).

b) (5RS)-{9-(3,5-bis-trifluoromethyl-benzoyl)-3-(1-methyl-piperidin-4-yl)-5-phenyl-1-oxa-3,9-diaza-spiro[5.5]undecan-2-one To a solution of 460 mg (1 mmol) [4-(2-amino-1-phenyl-ethyl)-4-hydroxy-piperidin-1-yl]-(3,5-bis-trifluoromethyl-phenyl)-methanone and 113 mg (1 mmol) of 1-methyl-4- piperidone in 1 ml of tetrahydrofurane 0.114 ml (2 mmol) acetic acid and 295 mg (1.4 mmol) sodium triacetoxyborohydride were added. The reaction mixture was shaken over night at room temperature. A solution of saturated sodium hydrogencarbonate was added, and the solution was extracted three times with dichloromethane. The combined organic phases were dried and evaporated under pressure. The residue was dissolved in 9 ml of tetrahydrofurane and 462 mg (2.85 mmol) 1,1'-carbonyl-diimidazole was added. The mixture was stirred under argon at room temperature over night and at 60° C. for three days. After cooling, water (5 ml) was added, and the solution was extracted three times with dichloromethane. The combined organic layers were dried and evaporated. The residue was purified by column chromatography ($SiO_2$, dichloromethane/methanol=90:10) to yield 388 mg (66%) of the title compound.

MS m/e (%): 583.1 (M+H$^+$, 100).

EXAMPLE 13

(5RS)-9-(3,5-bis-trifluoromethyl-benzoyl)-5-phenyl-3-(tetrahydro-pyran-4-yl)-1-oxa-3,9-diaza-spiro[5.5] undecan-2-one The title compound was obtained in comparable yields according to the procedures described for example 12 using tetrahydro-4H-pyran-4-one instead of 1-methyl-4-piperidone in step b).

MS m/e (%): 241.0 ($(CF_3)_2C_6H_3CHO$, 100); 570.0 (M$^+$, 2).

EXAMPLE 14

(5RS)-2-[9-(3,5-bis-trifluoromethyl-benzoyl)-2-oxo-5-phenyl-1-oxa-3,9-diaza-spiro[5.5]undec-3-yl]-N,N-dimethyl-acetamide To a solution of 243 mg (0.5 mmol) 9-(3,5-bis-trifluoromethyl-benzoyl)-5-phenyl-1-oxa-3,9-diaza-spiro [5.5]undecan-2-one in dimethylformamide 24 mg (0.5 mmol) of a 55% sodium hydride suspension in mineral oil was added at room temperature under argon. After 15 min, 126 mg (0.8 mmol) of 2-chloro-N,N-dimethylacetamide was added. The reaction mixture was stirred at 80° C. under argon overnight. After evaporation of the solvent in vacuum water (1 ml) was added and the mixture was extracted with ethyl acetate. The organic layer was dried over ($Na_2SO_4$) and concentrated. The residue was purified by column chromatography ($SiO_2$, Hexane/ethylacetate=1:1) to yield 154 mg (54%) of the title compound.

MS m/e (%): 572.1 (M+H$^+$, 100).

EXAMPLE 15

(5RS)-9-(3,5-bis-trifluoromethyl-benzoyl)-3-(2,2-difluoro-ethyl)-5-(3,4-difluoro-phenyl)-1-oxa-3,9-diaza-spiro[5.5]undecan-2-one To a solution of 261 mg (0.5 mmol) 9-(3,5-bis-trifluoromethyl-benzoyl)-5-(3,4-difluoro-phenyl)-1-oxa-3,9-diaza-spiro[5.5]undecan-2-one in dimethylformamide 24 mg (0.5 mmol) of a 55% sodium hydride suspension in mineral oil was added at room temperature under argon. After 15 min, 80 mg (0.55 mmol) of 2-bromo-1,1-difluoroethane was added. The reaction mixture was stirred at room temperature under argon overnight. After evaporation of the solvent in vacuum water (1 ml) was added and the mixture was extracted with ethyl acetate. The organic layer was dried over ($Na_2SO_4$) and concentrated. The residue was purified by column chromatography ($SiO_2$, Hexane/ethylacetate=1:1) to yield 96 mg (33%) of the title compound.

MS m/e (%): 587.1 (M+H$^+$, 100).

EXAMPLE 16

(5RS)-9-(3,5-bis-trifluoromethyl-benzoyl)-5-phenyl-3-pyridin-3-ylmethyl-1-oxa-3,9-diaza-spiro[5.5] undecan-2-one The title compound was obtained in comparable yields according to the procedures described for example 15 using 3-(chloromethyl)-pyridine hydrochloride instead of 2-bromo-1,1-difluoroethane and 9-(3,5-bis-trifluoromethyl-benzoyl)-5-phenyl-1-oxa-3,9-diaza-spiro[5.5]undecan-2-one instead of 9-(3,5-bis-trifluoromethyl-benzoyl)-5-(3,4-difluoro-phenyl)-1-oxa-3,9-diaza-spiro[5.5]undecan-2-one.

MS m/e (%): 578.1 (M+H$^+$, 100).

EXAMPLE 17

(5RS)-9-(3,5-bis-trifluoromethyl-benzoyl)-3-(4,6-dimethoxy-[1,3,5]triazin-2-yl)-5-phenyl- oxa-1-3,9-diaza-spiro[5.5]undecan-2-one The title compound was obtained in comparable yields according to the procedures described for example 15 using 2-chloro-4,6-dimethoxy-1,3,5-triazine instead of 2-bromo-1,1-difluoroethane, 9-(3,5-bis-trifluoromethyl-benzoyl)-5-phenyl-1-oxa-3,9-diaza-spiro[5.5]undecan-2-one instead of 9-(3,5-bis-trifluoromethyl-benzoyl)-5-(3,4-difluoro-phenyl)-1-oxa-3,9-diaza-spiro[5.5]undecan-2-one and dimethoxyethane instead of dimethylformamide.

MS m/e (%): 626.1 (M+H$^+$, 100).

EXAMPLE 18

(5RS)-9-(3,5-bis-trifluoromethyl-benzoyl)-3-methyl-5-phenyl-1-oxa-3,9-diaza-spiro[5.5]undecan-2-one The title compound was obtained in comparable yields according to the procedures described for example 15 using methyliodide instead of 2-bromo-1,1-difluoroethane, 9-(3,5-bis-trifluoromethyl-benzoyl)-5-phenyl-1-oxa-3,9-diaza-spiro[5.5]undecan-2-one instead of 9-(3,5-bis-trifluoromethyl-benzoyl)-5-(3,4-difluoro-phenyl)-1-oxa-3,9-diaza-Spiro[5.5]undecan-2-one and N-methylpyrrolidone instead of dimethylformamide.

MS m/e (%):241.0 ($(CF_3)_2C_6H_3CHO$, 100); 500.1 (M$^+$, 7).

EXAMPLE 19

(5RS)-9-(3,5-bis-trifluoromethyl-benzoyl)-5-(3,4-difluoro-phenyl)-3-(2-methoxy-ethyl)-1-oxa-3,9-diaza-spiro[5.5]undecan-2-one The title compound was obtained in comparable yields according to the procedures described for example 15 using 2-bromoethyl-methyl ether instead of 2-bromo-1,1-difluoroethane.

MS m/e (%): 581.0 (M+H$^+$, 100).

EXAMPLE 20

(5RS)-9-(3,5-bis-trifluoromethyl-benzoyl)-5-(3,4-difluoro-phenyl)-3-methyl-1-oxa-3,9-diaza-spiro[5.5]undecan-2-one The title compound was obtained in comparable yields according to the procedures described for example 15 using methyliodide instead of 2-bromo-1,1-difluoroethane.

MS m/e (%): 537.2 (M+H$^+$, 100).

EXAMPLE 21

(5RS)-9-(3,5-bis-trifluoromethyl-benzoyl)-3-(3-hydroxy-propyl)-5-phenyl-1-oxa-3,9-diaza-spiro[5.5]undecan-2-one To a solution of 2.43 g (5 mmol) 9-(3,5-bis-trifluoromethyl-benzoyl)-5-phenyl-1-oxa-3,9-diaza-spiro[5.5]undecan-2-one in N-methylpyrrolidone 0.436 g (0.5 mmol) of a 55% sodium hydride suspension in mineral oil was added at room temperature under argon. After 15 min. 1.27 g (5 mmol) of (3-bromopropoxy)-tert-butyldimethylsilane was added. The reaction mixture was stirred at 100° C. under argon overnight. After cooling a solution of saturated aqueous NaHCO$_3$ was added and the mixture was extracted with ethyl acetate. The organic layer was dried over (Na$_2$SO$_4$) and concentrated. The residue was purified by column chromatography (SiO$_2$, Hexane/ethylacetate=2:1) to yield 1.66 g (50%) of a yellow oil.

The oil was dissolved in a mixture of hydrochloric acid/ethanol and the solution was stirred at room temperature over night. The solvent was evaporated under vacuum and the residue was partitioned between dichloromethane and water. The organic layer was then washed two times with a solution of saturated aqueous NaHCO$_3$. The organic layer was dried over MgSO$_4$ and evaporated. The residue was purified by column chromatography (SiO$_2$, ethylacetate) to yield 0.83 g (30%) of the title compound.

MS m/e (%): 545.2 (M+H$^+$, 100).

EXAMPLE 22

(5RS)-9-(3,5-bis-trifluoromethyl-benzoyl)-3-(2-hydroxy-ethyl)-5-phenyl-1-oxa-3,9-diaza-spiro[5.5]undecan-2-one To a solution of 2.43 g (5 mmol) 9-(3,5-bis-trifluoromethyl-benzoyl)-5-phenyl-1-oxa-3,9-diaza-spiro[5.5]undecan-2-one in dimethylformamide 0.436 g (0.5 mmol) of a 55% sodium hydride suspension in mineral oil was added at room temperature under argon. After 30 min, 1.32 g (5.5 mmol) of (3-bromoethoxy)-tert-butyldimethylsilane was added. The reaction mixture was stirred at room temperature under argon overnight. After evaporation of the solvent, an aqueous saturated solution of NaHCO$_3$ was added and the solution was extracted with ethyl acetate. The organic layer was dried over (Na$_2$SO$_4$) and concentrated. The residue was purified by column chromatography (SiO$_2$, Hexane/ethylacetate=2:1) to yield 0.483 g (15%) of a white foam, which was dissolved in a mixture of hydrochloric acid/ethanol and stirred at room temperature overnight. The solvent was evaporated under vacuum and the residue was partitioned between dichloromethane and water. The organic layer was washed two times with a solution of saturated aqueous NaHCO$_3$. The organic layer was dried over MgSO$_4$ and evaporated to yield 0.395 g (15%) of the title compound.

MS m/e (%): 531.2 (M+H$^+$, 100).

EXAMPLE 23

(5RS)-9-(3,5-bis-trifluoromethyl-benzoyl)-5-phenyl-3-(3-pyrrolidin-1-yl-propyl)-1-oxa-3,9-diaza-spiro[5.5]undecan-2-one To a solution of 810 mg (1.49 mmol) 9-(3,5-bis-trifluoromethyl-benzoyl)-3-(3-hydroxy-propyl)-5-phenyl-1-oxa-3,9-diaza-spiro[5.5]undecan-2-one in dichloromethane (15 ml) 301 mg (2.98 mmol) of triethylamine were added at room temperature under argon. After cooling to 0° C., 187 mg (1.64 mmol) of methanesulfonyl chloride was added and the reaction mixture was stirred under argon for 90 min. Water was added and the organic layer was separated, dried (Na2SO4) and concentrated to give 904 mg (98%) of a white foam. The foam was dissolved in dimethylformamide, 243 mg of sodium hydrogencarbonate (2.9 mmol) and 155 mg (2.18 mmol) of pyrrolidine were added. The reaction mixture was shaken overnight at room temperature. After evaporation of the solvent, the residue was partitioned between water and ethylacetate. The two layers were separated and the organic layer was dried (Na$_2$SO$_4$) and evaporated. The residue was purified by column chromatography (SiO$_2$, dichloromethane/methanol=97:3) to give 239 mg (27%) of the title compound.

MS m/e (%): 598.0 (M+H$^+$, 100).

EXAMPLE 24

(5RS)-9-(3,5-bis-trifluoromethyl-benzoyl)-3-(3-morpholin-4-yl-propyl)-5-phenyl-1-oxa-3,9-diaza-spiro[5.5]undecan-2-one The title compound was obtained in comparable yields according to the procedures described for example 23 using morpholine instead of pyrrolidine.

MS m/e (%): 614.2 (M+H$^+$, 100).

EXAMPLE 25

(5RS)-9-(3,5-bis-trifluoromethyl-benzoyl)-3-(3-dimethylamino-4-yl-propyl)-5-phenyl-1-oxa-3,9-diaza-spiro[5.5]undecan-2-one The title compound was obtained in comparable yields according to the procedures described for example 23 using dimethylamine instead of pyrrolidine.

MS m/e (%): 572.2 (M+H$^+$, 100).

EXAMPLE 26

(5RS)-9-(3,5-bis-trifluoromethyl-benzoyl)-3-[3-(3-hydroxy-pyrrolidin-1-yl)-propyl]-5-phenyl-1-oxa-3,9-diaza-spiro[5.5]undecan-2-one The title compound was obtained in comparable yields according to the procedures described for example 23 using (R)-3-hydroxypyrrolidine instead of pyrrolidine.

MS m/e (%): 614.2 (M+H$^+$, 100).

EXAMPLE 27

(5RS)-9-(3,5-2is-trifluoromethyl-benzoyl)-3-(2-morpholin-4-yl-ethyl)-5-phenyl-1-oxa-3,9-diaza-spiro[5.5]undecan-2-one hydrochloride The title compound was obtained in comparable yields according to the procedures described for example 23 using morpholine instead of pyrrolidine and 9-(3,5-bis-trifluoromethyl-benzoyl)-3-(2-hydroxy-ethyl)-5-phenyl-1-oxa-3,9-diaza-spiro[5.5]undecan-2-one instead of 9-(3,5-bis-trifluoromethyl-benzoyl)-3-(3-hydroxy-propyl)-5-phenyl-1-oxa-3,9-diaza-spiro[5.5]undecan-2-one and subsequent treatment with hydrochloric acid in ethanol.

MS m/e (%): 600.1 (M+H$^+$, 100).

EXAMPLE 28

(5RS)-9-(3,5-bis-trifluoromethyl-benzoyl)-3-(2-dimethylamino-ethyl)-5-phenyl-1-oxa-3,9-diaza-spiro[5.5]undecan-2-one hydrochloride The title compound was obtained in comparable yields according to the procedures described for example 23 using dimethylamine instead of pyrrolidine and 9-(3,5-bis-trifluoromethyl-benzoyl)-3-(2-hydroxy-ethyl)-5-phenyl-1-oxa-3,9-diaza-spiro[5.5]undecan-2-one instead of 9-(3,5-bis-trifluoromethyl-benzoyl)-3-(3-hydroxy-propyl)-5-phenyl-1-oxa-3,9-diaza-spiro[5.5]undecan-2-one and subsequent treatment with hydrochloric acid in ethanol.

MS m/e (%): 558.3 (M+H$^+$, 100).

EXAMPLE 29

(5RS)-9-(3,5-bis-trifluoromethyl-benzoyl)-3-[3-(4-methyl-piperazin-1-yl)-propyl]-5-phenyl-1-oxa-3,9-diaza-spiro[5.5]undecan-2-one The title compound was obtained in comparable yields according to the procedures described for example 23 using 4-methyl-piperazine instead of pyrrolidine MS m/e (%): 627.2 (M+H$^+$, 100).

EXAMPLE 30

(5RS)-9-(3,5-bis-trifluoromethyl-benzoyl)-5-phenyl-3-(2-pyrrolidin-1-yl-ethyl)-1-oxa-3,9-diaza-spiro[5.5]undecan-2-one; hydrochloride The title compound was obtained in comparable yields according to the procedures described for example 23 using 9-(3,5-bis-trifluoromethyl-benzoyl)-3-(2-hydroxy-ethyl)-5-phenyl-1-oxa-3,9-diaza-spiro[5.5]undecan-2-one instead of 9-(3,5-bis-trifluoromethyl-benzoyl)-3-(3-hydroxy-propyl)-5-phenyl-1-oxa-3,9-diaza-spiro[5.5]undecan-2-one and subsequent treatment with hydrochloric acid in ethanol.

MS m/e (%): 584.2 (M+H$^+$, 100).

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:
1. A compound of formula I

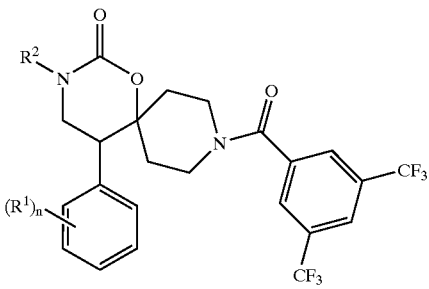

wherein
(R$^1$)$_n$ is independently from each other halogen, lower alkyl or lower alkoxy;
R$^2$ is hydrogen, lower alkyl, lower halogen-alkyl, —(CH$_2$)$_m$—OH, —(CH$_2$)$_m$—NR$_2$, —(CH$_2$)$_m$O-lower alkyl, —(CH$_2$)$_m$—C(O)—NR$_2$, or is —(CH$_2$)$_m$-6-membered heteroaryl selected from the group consisting of triazinyl, pyridinyl, pyrazinyl, pyrimidinyl or pyradizinyl, optionally substituted by one or more lower alkoxy, —(CH$_2$)$_m$-5 or 6-membered non aromatic heterocyclyl selected from the group consisting of pyrrolidinyl, imidazolidinyl, tetrahydro-pyranyl, piperidyl, piperazinyl or morpholinyl, optionally substituted by hydroxy or lower alkyl;
R is hydrogen or lower alkyl and may be the same or different in case of R$_2$;
n is 0, 1, or 2;
m is 0, 1, 2, 3 or 4;
or a pharmaceutically acceptable acid addition salt thereof.

2. The compound of claim 1, wherein R$^2$ is hydrogen.

3. The compound of claim 2, wherein the compound is selected from the group consisting of:

(5RS)-9-(3,5-bis-trifluoromethyl-benzoyl)-5-(3-chloro-phenyl)-1-oxa-3,9-diaza-spiro[5.5]undecan-2-one, (5RS)-9-(3,5-bis-trifluoromethyl-benzoyl)-5-(3,4-difluoro-phenyl)-1-oxa-3,9-diaza-spiro[5.5]undecan-2-one, (5RS)-9-(3,5-bis-trifluoromethyl-benzoyl)-5-(3,4-dichloro-phenyl)-1-oxa-3,9-diaza-spiro[5.5]undecan-2-one, (5RS)-9-(3,5-bis-trifluoromethyl-benzoyl)-5-phenyl-1-oxa-3,9-diaza-spiro[5.5]undecan-2-one, (5RS)-9-(3,5-bis-trifluoromethyl-benzoyl)-5-(2,3-difluoro-phenyl)-1-oxa-3,9-diaza-spiro[5.5]undecan-2-one and (5RS)-9-(3,5-bis-trifluoromethyl-benzoyl)-5-(2,5-difluoro-phenyl)-1-oxa-3,9-diaza-spiro[5.5]undecan-2-one.

4. The compound of claim 1, wherein R$^2$ is a —(CH$_2$)$_m$-6-membered heteroaryl group, optionally substituted by one or more lower alkoxy.

5. The Compounds of claim 4, wherein the compound is selected from the group consisting of:

(5RS)-9-(3,5-bis-trifluoromethyl-benzoyl)-5-phenyl-3-pyridin-3-yl-methyl-1-oxa-3,9-diaza-spiro[5.5]undecan-2-one and (5RS)-9-(3,5-bis-trifluoromethyl-benzoyl)-3-(4,6-dimethoxy-[1,3,5]triazin-2-yl)-5-phenyl-1-oxa-3,9-diaza-spiro[5.5]undecan-2-one.

6. The compound of claim 1, wherein R$^2$ is —(CH$_2$)$_m$—C(O)—N(CH$_3$)$_2$.

7. The compound of claim 6, wherein the compound is (5RS)-2-[9-(3,5-bis-trifluoromethyl-benzoyl)-2-oxo-5-phenyl-1-oxa-3,9-diaza-spiro[5.5]undec-3-yl]-N,N-dimethyl-acetamide.

8. The compound of claim 1, wherein R$^2$ is —(CH$_2$)$_m$—OH.

9. The compounds of claim 8, wherein the compound is selected from the group consisting of:

(5RS)-9-(3,5-bis-trifluoromethyl-benzoyl)-3-(3-hydroxy-propyl-5-phenyl-1-oxa-3,9-diaza-spiro[5.5]undecan-2-one; and (5RS)-9-(3,5-bis-trifluoromethyl-benzoyl)-3-(2-hydroxy-ethyl)-5-phenyl-1-oxa-3,9-diaza-spiro[5.5]undecan-2-one.

10. The compounds of claim 1, wherein R$^2$ is a —(CH$_2$)$_m$-5 or 6-membered non aromatic heterocyclyic group, optionally substituted by hydroxy or lower alkyl.

11. The compounds of claim 10, wherein the compound is selected from the group consisting of:

(5RS)-9-(3,5-bis-trifluoromethyl-benzoyl)-3-(1-methyl-piperidin-4-yl)-5-phenyl-1-oxa-3,9-diaza-spiro[5.5]undecan-2-one, (5RS)-9-(3,5-bis-trifluoromethyl-benzoyl)-5-phenyl-3-(3-pyrrolidin-1-yl-propyl)-1-oxa-3,9-diaza-spiro[5.5]undecan-2-one, (5RS)-9-(3,5-bis-trifluoromethyl-benzoyl)-3-(3-morpholin-4-yl-propyl)-5-phenyl-1-oxa-3,9-diaza-spiro[5.5]undecan-2-one, (5RS)-9-(3,5-bis-trifluoromethyl-benzoyl)-3-[3-(3-hydroxy-pyrrolidin-1-yl)-propyl]-5-phenyl-1-oxa-3,9-diaza-spiro[5.5]undecan-2-one and (5RS)-9-(3,5-2is-trifluoromethyl-benzoyl)-3-(2-morpholin-4-yl-ethyl)-5-phenyl-1-oxa-3,9-diaza-spiro[5.5]undecan-2-one.

12. The compound of claim 1, wherein R$^2$ is —(CH$_2$)$_m$—NR$_2$.

13. The compounds of claim 12, wherein the compound is selected from the group consisting of:

(5RS)-9-(3,5-bis-trifluoromethyl-benzoyl)-3-(3-dimethylamino-4-yl-propyl)-5-phenyl-1-oxa-3,9-diaza-spiro[5.5]undecan-2-one, and (5RS)-9-(3,5-bis-trifluoromethyl-benzoyl)-3-(2-dimethylamimo-ethyl)-5-phenyl-1-oxa-3,9-diaza-spiro[5.5]undecan-2-one.

14. A pharmaceutical composition comprising a compound of claim 1 and a pharmaceutically acceptable excipient.

15. A process for preparing a compound of claim 1, which process comprises a) cyclizing a compound of formula

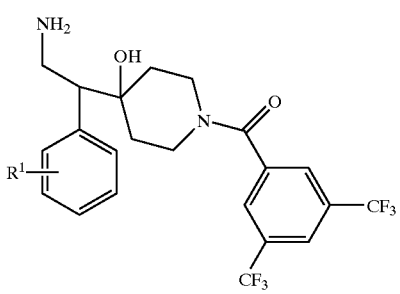

to a compound of the formula

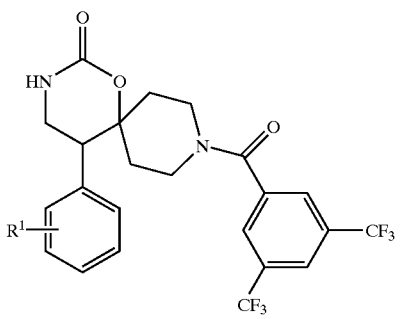

wherein R¹ has the significances given in claim 1, or b) reacting a compound of formula

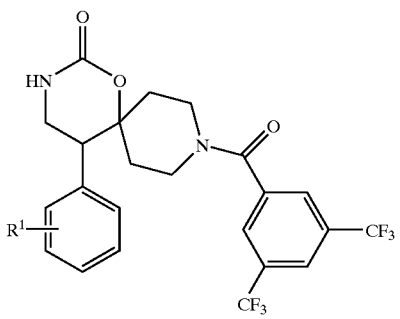

with

R²—X to a compound of formula

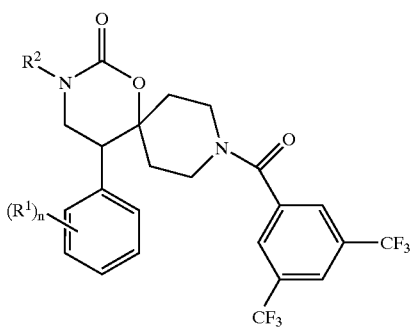

wherein $R^1$ and $R^2$ have the significances given in claim 1 and X is halogen, or c) reacting a compound of formula

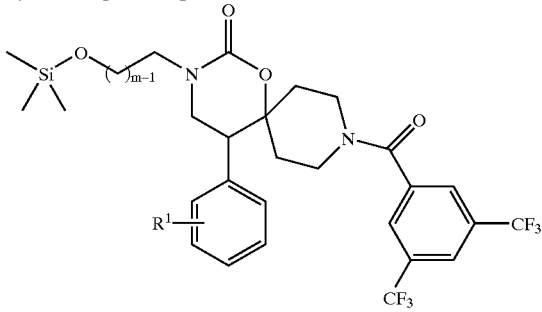

to a compound of the formula

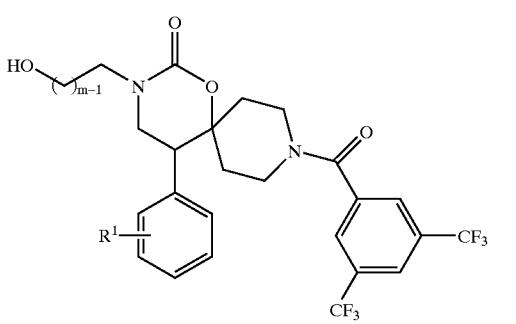

and wherein m and $R^1$ are described in claim 1, or d) reacting a compound of formula

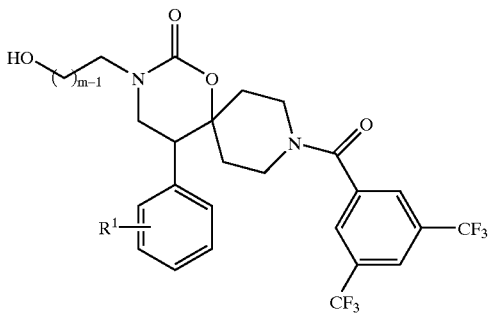

with a compound of the formula

R₂NH to a compound of the formula

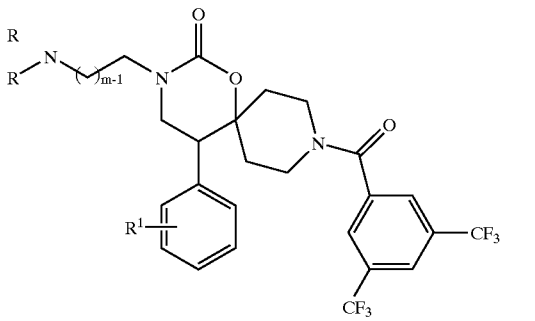

wherein the definition for $R^1$ is given in claim 1, and R is hydrogen or lower alkyl, or e) reacting a compound formula

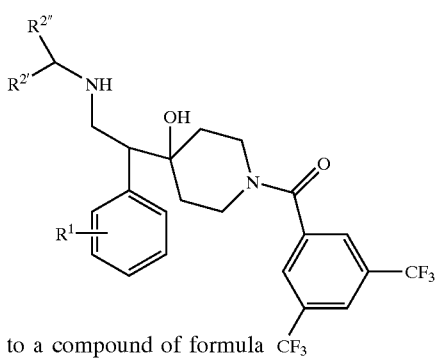

to a compound of formula

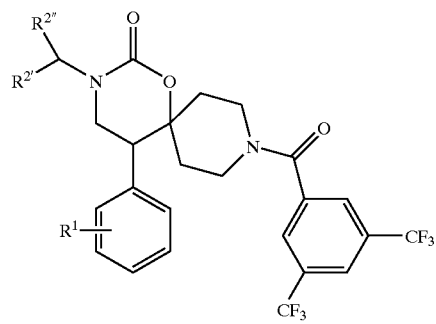

wherein $R^1$, is described in claim 1 and $R^{2'}$ and $R^{2''}$ is hydrogen, alkyl, aryl, heteroaryl or taken together a nonaromatic carbocyclic or heterocyclic ring, optionally substituted by halogen, hydroxy, lower alkoxy or lower alkyl, and optionally, converting the compound obtained into a pharmaceutically acceptable acid addition salt.

16. A method for treating a disease related to NK-1 receptor agonists, the disease selected from anxiety, depression, psychosis, urinary incontinence, motion sickness and emesis, the method comprising administering to a patient in need thereof a compound of claim 1.

* * * * *